United States Patent [19]

Crawford

[11] Patent Number: 4,848,346

[45] Date of Patent: Jul. 18, 1989

[54] PACEMAKER CONNECTOR SYSTEM

[75] Inventor: Keith F. Crawford, Valencia, Calif.

[73] Assignee: Siemens-Pacesetter, Inc., Sylmar, Calif.

[21] Appl. No.: 128,001

[22] Filed: Dec. 2, 1987

[51] Int. Cl.4 .......................... A61N 1/00; H05G 00/00
[52] U.S. Cl. .................................................. 128/419 P
[58] Field of Search ..................... 128/419 P, 419 PG;
439/816, 817, 818, 819, 820, 824

[56] References Cited

U.S. PATENT DOCUMENTS

| Re. 31,990 | 9/1985 | Sluetz et al. | 128/419 P |
| 4,180,078 | 12/1979 | Anderson | 128/419 P |
| 4,461,194 | 7/1984 | Moore | 128/419 P |

Primary Examiner—Francis Jaworski
Assistant Examiner—George Manuel
Attorney, Agent, or Firm—Bryant R. Gold; Leslie S. Miller

[57] ABSTRACT

A pacemaker connector system for the coaxial heart lead of a bipolar pacemaker consists of two connector block assemblies housing circular springs which circumferentially grip the central and outer terminals of the lead. Protruding ends of the springs are covered by rubber septum buttons which, when depressed, open the spring interiors to allow insertion of the heart lead. The problems associated with set screw systems are eliminated, and improved mechanical and electrical contact over other types of spring systems is provided.

22 Claims, 3 Drawing Sheets

PACEMAKER CONNECTOR SYSTEM

This invention relates to a method for connecting a pacemaker heart lead to a pacemaker and, more particularly, to providing a connection system in which the lead conductor is gripped circumferentially by an annular compression spring.

BACKGROUND OF THE INVENTION

Cardiac pacemakers are electrical devices that function to regulate the pace of the heartbeat. These vital therapeutic devices are surgically implanted in the patient's body, where they may remain for years. A typical implanted pacemaker operates by furnishing, through an electrical lead attached to the ventricle of the heart, stimulation pulses which the heart is not providing. Generally there are two types of electrode systems used in cardiac pacing. The bipolar system of operation makes use of two electrodes situated near the tip of a lead which is placed into the heart; the electrodes are typically rings which conduct the stimulus pulse and sense natural cardiac signals. A unipolar electrode arrangement makes use of a single electrode placed on the lead, generally near the tip, and another electrode at a location remote from the electrode tip with the return current path being through body tissues. The other electrode is most often a portion of the pacemaker housing; this conveniently provides an electrode of large surface area contacting the body. Alternatively, the other electrode can be on the lead itself proximal to the tip electrode.

The attachment of the heart lead to the pulse generator unit is an important step in pacemaker implantation. Problems with the connection are relatively common, with attendant pacemaker malfunctioning. For many years the connector system for a pacemaker has conventionally consisted of a plastic "connector top" with molded-in terminal blocks containing set screws.

Modern pacemaker leads are coaxial; they are plugged into the terminal receptacles in the pacemaker and are secured by tiny allen head set screws which hold the lead terminals in position and also provide the necessary electrical contacts. Terminal wires extending through hermetic feedthrough elements into the body of the pacemaker are resistance welded to blocks in which the set screws are mounted. The set screws are supposed to be torqued at a level of about 18 inch-ounces.

Drawbacks to the set screw connector system have included: (a) a specially designed wrench is necessary for tightening the set screw; (b) the set screw threads may be stripped due to overtightening; and (c) the set screw must be sealed from body fluids after tightening.

The set screw type of construction presents other problems as well. One is that the set screw sometimes protrudes into the bore of the connector to a point where it blocks the proper insertion of the pacemaker lead. A physician attempting to attach the heart lead to the generating unit may attempt to force the lead terminal into the blocked bore produced by a protruding set screw. Frustration of the physician as well as more serious problems are likely to occur.

Another problem results from overtorquing of the set screw with a lead terminal in position. The set screw that bears against the outer ring of a coaxial lead termination may deform the ring to the point where it is impossible to withdraw the lead terminal from the pacemaker housing. When the time comes for replacement of the pacemaker it may be necessary to actuall cut the leads so that the pacemaker can be removed. In that event not only must the pacemaker be replaced, but also the heart lead as well.

As an alternative to the set screw method of connection, various manufacturers have developed connector systems that use various types of spring contacts. The springs are typically small fingers which contact the heart lead terminals. Success has been limited with such designs primarily because of less-than-satisfactory mechanical contact. Electrical contact is also less than optimal because it is made at specific points around the lead terminal rather than over a large contact surface area.

SUMMARY OF THE INVENTION

A simple solution to the problems presented by conventional pacemaker connector systems is provided by the circumferential spring-gripping connector of the present invention, which includes a metal connector block, a compression spring, and a plastic retainer. The compression spring is shaped roughly like the lower-case Greek letter sigma ($\sigma$), with an open ring-shaped portion and a straight extension beyond where a ring would have closed. The spring is spot welded into a recess in the metal connector block surrounding a cylindrical bore. The plastic retainer mates with the connector block to hold the spring in place.

The spring extension arm protrudes from the assembly in a slot to the outside. The inside diameter of the spring in its relaxed state is smaller than the outside diameter of the heart lead terminal. When the extension arm on the spring is pressed, however, the spring inner diameter increases to accommodate insertion of the heart lead terminal. After the heart lead has been inserted, release of the spring arm causes the compression spring to close around the heart lead terminal. The result is a circumferential mechanical gripping of the heart lead terminal with a large amount of contact surface area. As a consequence, the electrical contact provided is far superior to, and more reliable than, any type of point contact.

The plastic retainer is glued into the connector block to insure proper and consistent alignment of the compression spring. The entire assembly is molded into the plastic connector top of the pacemaker. The compression spring arm is substantially flush with the side of the plastic connector top of the pacemaker, and a rubber septum is provided to cover the end of the arm. The septum is glued into place to provide a barrier between the metal components of the compression spring connector system and body fluids. It also serves as a 'push button' for expanding the comprssion spring to connect or disconnect the heart lead terminal. A connector system comprising two block-spring-retainer assemblies may be used to provide connection to coaxial-type heart lead systems or four block-spring-retainer assemblies to connect to two coaxial leads (both atrial and ventricle).

BRIEF DESCRIPTION OF THE DRAWING

The above and other objects, features and advantages of the present invention will be more apparent from the following more particular description thereof presented in conjunction with the accompanying drawings, wherein.

DESCRIPTION OF THE PREFERRED EMBODIMENT

Figure 1:
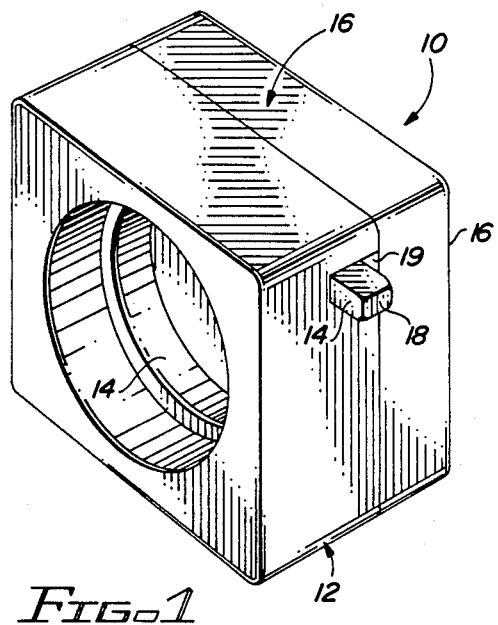
FIG. 1 is a perspective view of the circumferentially gripping connector block assembly of the present invention.

FIG. 1 shows a connector block assembly 10 in accordance with the present invention. A conductive connector block 12 houses a compression spring 14 which is shaped like a lower-case Greek letter sigma. A plastic retainer 16 is glued into connector block 12 to ensure proper and consistent alignment of the compression spring 14. A straight end portion 18 of compression spring 14 extends through a slot 19 in connector block 12 to the outside.

Figure 2A:
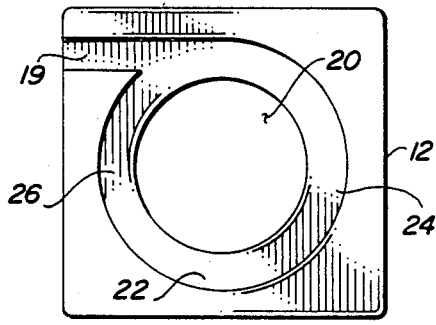
FIG. 2A is a side view and FIG. 2B is a partially broken-away end view of the connector block of FIG. 1.
Figure 2B:
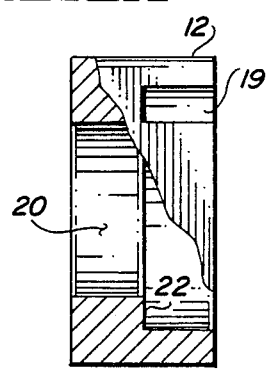

The details of connector block 12 are shown in FIGS. 2A and 2B, which are end and side views, respectively, of connector block 12. FIG. 2A shows that connector block 12 has a central circular aperture 20 surrounded by a substantially circular recess 22 into which compression spring 14 fits. The width of recess 22 is wider on the side marked 24 than at the side marked 26.

Figure 3A:
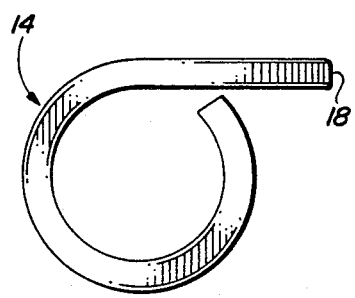
FIG. 3A is a side view and FIG. 3B is an end view of the compression spring mounted within the connector block of FIG. 2.
Figure 3B:
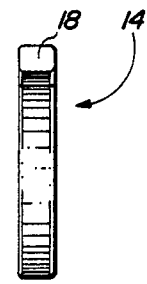

Compression spring 14 is spot welded in the vicinity of 26 to connector block 12. Side and end views of compression spring 14 are shown in FIGS. 3A and 3B, respectively. When spring 14 is welded into place in recess 22 of connector block 12, a force applied to end portion 18 of spring 14 causes the inner diameter of spring 14 to increase. This is allowed by the shape of recess 22, which is wider at 24 than at 26.

Figure 4A:
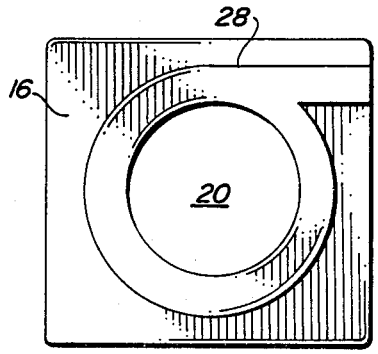
FIG. 4A is a side view and FIG. 4B is a partially broken-away end view of a retainer for the connector block.
Figure 4B:
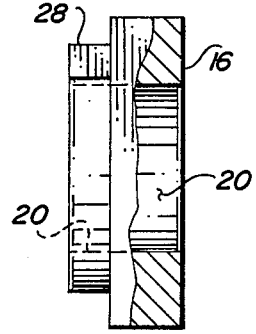

As shown in FIG. 4A, retainer 16 has a plug portion 28 surrounding aperture 20. Plug portion 28 is shaped to fit into recess 22 of connector block 12. FIG. 4B is an end view of retainer 16 which, when considered with FIG. 2B, shows how retainer 16 has a shape that mates with that of connector block 12.

Figure 5:
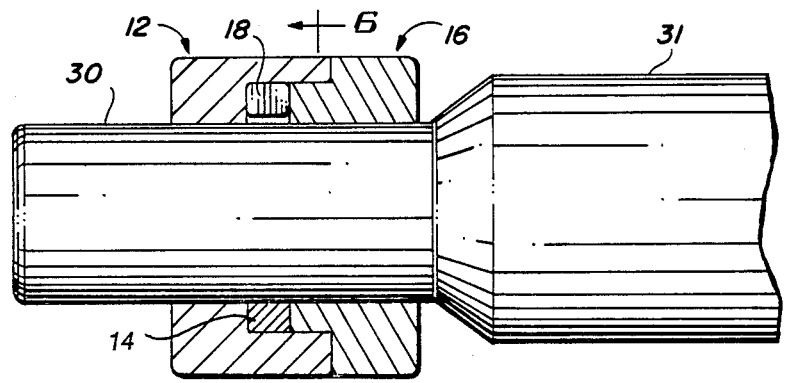
FIG. 5 is a sectional end view of a heart lead held in place by a connector block assembly.
Figure 6:
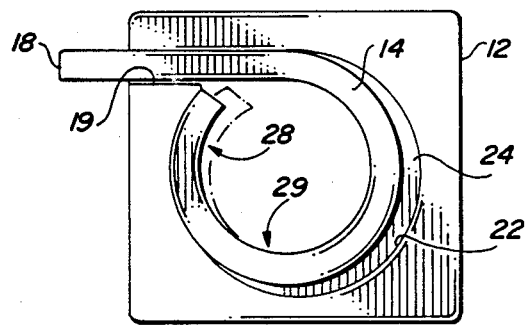
FIG. 6 is a sectional view taken along the line 6-6 of FIG. 5.

In FIGS. 5 and 6, compression spring 14 is shown residing in recess 22 of connector block 12. Spring 18 is spot welded to connector block 12 at points 28 and 29, and the extra room for expansion at 24 when straight portion 18 of spring 14 is pressed allows the interior portion of spring 14 to open up. In FIG. 5 the end conductor 30 of a heart lead 31 is shown after insertion through the central part of spring 14. Since the diameter of end terminal 30 is larger than the inner diameter of spring 14 in its relaxed state, spring 14 grips terminal 30 over a large part of its circumference. There is a correspondingly large area of contact between terminal 30 and spring 14. Both spring 14 and connector block 12 are preferably made from 316L stainless steel.

Figure 7:
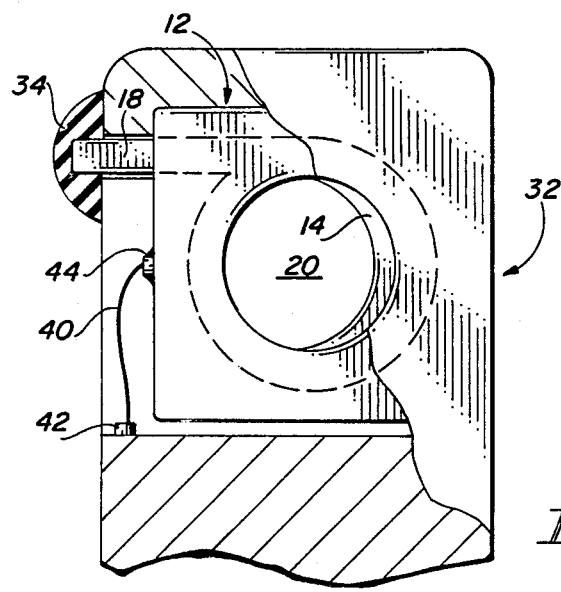
FIG. 7 is an end view, partially broken away, of a connector block assembly in a pacemaker case.

FIG. 7 shows a spring-loaded connector block assembly such as has been described above, molded into the plastic connector 32 of a pacemaker. As shown in the partially broken away end view of FIG. 7, spring 14 partially obstructs the bore of aperture 20 in connector block 12. Straight portion 18 of spring 14 extends through slot 30 to the outside of plastic connector top 32. A rubber septum button 34 covers the slightly protruding end of straight portion 18 of spring 14. Rubber septum button 34, which is glued into place, provides a barrier between the metal components of the connector block assembly and body fluids. It also serves as a flexible "push button" which when depressed allows the insertion of a heart lead terminal through the expanded inner diameter of spring 14. When button 34 is released, spring 14 grips the inserted terminal around most of its circumference to provide excellent mechanical gripping and electrical conducting contact. A lead 40 is shown extending from a feedthrough element 42 in the pacemaker case to a point 44 where it is resistance welded to the connector block 12.

Figure 8:
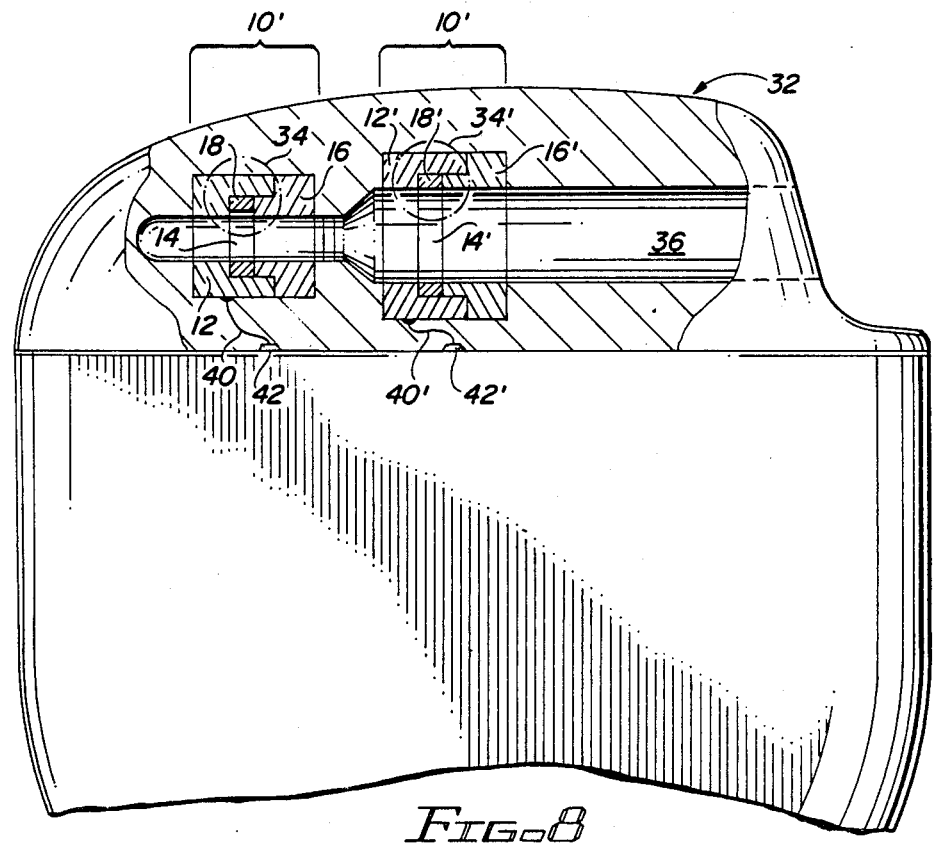
FIG. 8 is a sectional side view of a pacemaker connector arrangement in accordance with the present invention.

FIG. 8 is a sectional side view of a connector system according to the present invention for a bipolar coaxial heart lead. Two sets of spring-loaded connector block assemblies 10 and 10' are shown spaced apart and molded into a plastic connector top 32 of a pacemaker. Connector block assembly 10 is dimensioned to accept the insertion of the distal tip of the centerl terminal of a heart lead. Connector block assembly 10' has a larger bore to accept the insertion of a ring terminal proximal to the center conductor tip. Compression springs 14 and 14' must be opened up simultaneously as the heart lead is inserted into bore 36 of plastic connector top 32 and then through the apertures in connector block assemblies 10 and 10'. This can be accomplished effectively by having the straight portions 18 and 18' extend outwardly through opposite sides of the top 32 so that a convenient thumb and finger opposed squeezing force may be applied to open both springs 14, 14' together. One spring is larger than the other, as shown, to accommodate ring and tip electrodes.

Figure 9:
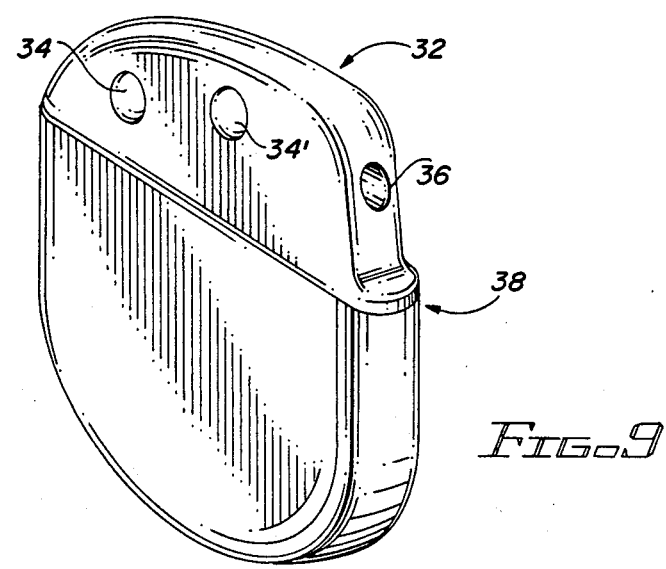
FIG. 9 is a perspective view of a pacemaker case embodying the connector system of the present invention.

FIG. 9 is a perspective view of a pacemaker generator 38 incorporating a connector system according to the present invention for a bipolar heart lead. Septum buttons 34 and 34' are pressed simultaneously to allow insertion of the bipolar heart lead into bore 36 in the pacemaker case. Alternatively, connector blocks 12 and 12' could be oriented in such a way that the protruding portions 18 and 18' of springs 14 and 14' would be on opposite sides of the pacemaker top 32, as described above. As noted, this has the advantage that septum buttons 34 and 34' situated on opposed sides of connector top 32 could be simultaneously depressed by a natural squeezing motion of the hand.

Retainer 16 is preferably made of a polysulfone plastic. Although compression spring 14 is shown in the drawings as being of square wire, the wire could as well be circular in cross section.

Although there has been described above one specific arrangement of a pacemaker connector system in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A pacemaker connector system comprising:
a connector block attached to a pacemaker, said connector block having a first aperture therein, said aperture defining a generally circular bore adapted to accept a pacemaker lead;
a retainer mating with said connector block and having a second aperture therethrough, also adapted to accept a pacemaker lead and being aligned with said first aperture in said connector block; and
a generally annular unclosed ring spring member with a projecting generally straight end portion extending about and partially obstructing said bore when in a relaxed state but capable of being expanded to a size larger than said pacemaker lead by the application of force to an end of said generally straight end portion.

2. The system of claim 1 wherein said connector block is of a conducting material and further including an electrical lead coupled to the connector block and extending to said pacemaker.

3. The system of claim 2 wherein said connector block is metallic and is welded to said electrical lead and to said spring member.

4. The system of claim 3 wherein at least the generally annular portion of the spring member is positioned within the connector block and is attached thereto at a portion of the ring which is remote from the generally straight end portion.

5. The system of claim 4 wherein the connector block defines an interior space configured to permit expansion of the annular ring portion upon the application of a generally tangential force along the straight end portion.

6. The system of claim 5 wherein said space is configured to permit expansion of the generally annular ring portion from a size smaller than said pacemaker lead to a size larger than said pacemaker lead, whereby the annular ring spring member is capable of receiving the pacemaker lead and gripping said lead with a strong mechanical and electrical connection thereto.

7. A pacemaker connector system comprising:
a generally sigma-shaped spring having an open ring annular portion and a generally straight extension for expanding the annular portion upon the application of a generally tangential force along said extension;
a connector attached to a pacemaker, said connector block block enclosing and connected to said spring, the block defining a first aperture therein sized to receive a pacemaker lead electrode for coupling to said spring, the annular portion of the spring being smaller than said electrode but expandable within said block to admit said electrode; and
a retainer having an aperture therethrough corresponding to said first aperture and aligned therewith for retaining the spring within said connector block.

8. The system of claim 7 wherein said connector block is of a conducting material and further including an electrical lead coupled to the connector block and extending to said pacemaker.

9. The system of claim 8 wherein said connector block is metallic and is welded to said electrical lead and to said spring.

10. The system of claim 9 wherein at least the generally annular portion of the spring is positioned within the connector block and is attached thereto at a portion of the spring which is remote from the generally straight extension.

11. The system of claim 10 wherein the connector block defines an interior space configured to permit expansion of the annular portion upon the application of a generally tangential force along the straight extension.

12. The system of claim 11 wherein said space is configured to permit expansion of the open ring annular portion from a size smaller than said pacemaker lead to a size larger than said pacemaker lead, whereby the annular portion is capable of readily receiving the pacemaker lead and gripping said pacemaker lead with a strong mechanical and electrical connection thereto.

13. The pacemaker connector system of claim 7 wherein said extension protrudes outside said connector block and further comprising flexible sealing means covering the end of the extension of said spring protruding outside said conductor block.

14. A pacemaker connector system for coaxial bipolar leads comprising:
a first circumferentially spring-gripping connector block assembly attached to a pacemaker, said connector block assembly adapted for accepting and holding the distal end of a center lead; and
a second circumferentially spring-gripping connector block assembly adapted for accepting and holding an outer lead concentric with said center lead and spaced apart from the distal end thereof, both of said assemblies having means for establishing spring-releasable electrical connections from said pacemaker to said leads.

15. The pacemaker connector system of claim 14 in which said first and second connector block assemblies each comprise:
a circumferentially gripping spring;
a conducting connector block defining an aperture and a circumferential recess therein in which said spring is housed and to which said spring is electrically connected, with an end portion of said spring protruding therefrom; and
a retainer having an aperture therethrough coaxial with said aperture in said connector block, said retainer having a plug portion with a shape mating with said recess in said connector block, said retainer fitting inside said connector block to enclose said spring;
whereby a lead inserted into said connector block may be gripped circumferentially by said spring.

16. The pacemaker connector system of claim 15 wherein said ends of said first and second springs protrude in opposing directions from said first and second connector block assemblies, so that said springs contained in said first and second connector block assemblies may be simultaneously expanded by application of a squeezing force exerted on said ends of said springs.

17. The pacemaker connector system of claim 15 wherein each of said spring is substantially sigma-shaped.

18. The pacemaker connector system of claim 17 wherein each of said spring has a rectangular cross section.

19. The pacemaker connector system of claim 17 wherein each of said spring is made from 316L stainless steel.

20. The pacemaker connector system of claim 15 wherein each of said retainer is made of polysulfone plastic.

21. The pacemaker connector system of claim 15 wherein a portion of each spring is spot welded to an interior wall of said recess in said connector block.

22. The pacemaker connector system of claim 15 wherein each plastic retainer is glued into a corresponding connector block and each protruding end of a spring is covered by a rubber septum.

* * * * *